(12) United States Patent
Gunther et al.

(10) Patent No.: US 10,709,354 B2
(45) Date of Patent: Jul. 14, 2020

(54) GENERATING A BREATHING ALERT

(71) Applicant: Photorithm, Inc., Smithfield, UT (US)

(72) Inventors: Jacob Gunther, North Logan, UT (US); Nathan E. Ruben, Smithfield, UT (US)

( * ) Notice: Subject to any disclaimer, the term of this patent is extended or adjusted under 35 U.S.C. 154(b) by 232 days.

(21) Appl. No.: 15/697,220

(22) Filed: Sep. 6, 2017

(65) Prior Publication Data
US 2018/0064369 A1   Mar. 8, 2018

Related U.S. Application Data

(60) Provisional application No. 62/383,769, filed on Sep. 6, 2016.

(51) Int. Cl.
| G06K 9/00 | (2006.01) |
| A61B 5/087 | (2006.01) |
| A61B 5/113 | (2006.01) |
| A61M 16/00 | (2006.01) |
| A61B 5/00 | (2006.01) |
| A61B 5/08 | (2006.01) |

(52) U.S. Cl.
CPC ............ *A61B 5/0873* (2013.01); *A61B 5/113* (2013.01); *A61B 5/4806* (2013.01); *A61B 5/746* (2013.01); *A61M 16/0051* (2013.01); *A61M 16/026* (2017.08); *A61B 5/0816* (2013.01); *A61M 2205/3375* (2013.01); *A61M 2205/502* (2013.01); *A61M 2205/584* (2013.01); *A61M 2230/63* (2013.01)

(58) Field of Classification Search
CPC ............ G06F 16/786; A61M 2205/18; A61M 2230/42; G08B 21/02; G08B 21/0476; G08B 13/196
See application file for complete search history.

(56) References Cited

U.S. PATENT DOCUMENTS

| 4,273,596 | A | * | 6/1981 | Gutierrez | .......... | H01L 27/14875 |
| | | | | | | 257/E27.16 |
| 6,352,517 | B1 | * | 3/2002 | Flock | ..................... | A61B 3/113 |
| | | | | | | 600/558 |
| 8,792,969 | B2 | * | 7/2014 | Bernal | ................... | A61B 5/091 |
| | | | | | | 600/476 |
| 2011/0251493 | A1 | * | 10/2011 | Poh | ........................ | G06K 9/624 |
| | | | | | | 600/477 |
| 2011/0305388 | A1 | * | 12/2011 | Wedi | ....................... | G06T 5/005 |
| | | | | | | 382/165 |
| 2012/0289850 | A1 | * | 11/2012 | Xu | ........................ | A61B 5/015 |
| | | | | | | 600/529 |
| 2013/0035599 | A1 | * | 2/2013 | De Bruijn | ............ | A61B 5/1135 |
| | | | | | | 600/476 |
| 2013/0342670 | A1 | * | 12/2013 | Kyal | .................... | A61B 5/7225 |
| | | | | | | 348/77 |

(Continued)

*Primary Examiner* — Guillermo M Rivera-Martinez
(74) *Attorney, Agent, or Firm* — Kunzler Bean & Adamson

(57) ABSTRACT

For generating a breathing alert, a method captures a video stream of a subject. The method further generates a vector time series that includes a vector for each image frame of the video stream. The method estimates of breathing signal from the vector time series. The method further determines one of large-scale motion and a breathing event of the subject based on the breathing signal. The method generates an alert if no breathing event is identified and no large-scale motion of the subject is identified within an event time interval.

21 Claims, 19 Drawing Sheets

(56) References Cited

U.S. PATENT DOCUMENTS

| | | | |
|---|---|---|---|
| 2014/0029824 A1* | 1/2014 | Shi | G06T 11/005 |
| | | | 382/131 |
| 2015/0245787 A1* | 9/2015 | Kyal | A61B 5/1128 |
| | | | 600/476 |
| 2015/0324636 A1* | 11/2015 | Bentley | G11B 27/17 |
| | | | 386/227 |
| 2015/0342535 A1* | 12/2015 | Chen | A61B 5/024 |
| | | | 600/476 |
| 2016/0089041 A1* | 3/2016 | Keat | A61B 5/72 |
| | | | 600/479 |
| 2016/0106340 A1* | 4/2016 | Mestha | A61B 5/0816 |
| | | | 600/476 |
| 2016/0343135 A1* | 11/2016 | De Haan | A61B 5/0077 |
| 2016/0371833 A1* | 12/2016 | Prasad | G06T 7/0012 |
| 2017/0042488 A1* | 2/2017 | Muhsin | A61B 5/742 |
| 2017/0119304 A1* | 5/2017 | Jeanne | A61B 5/7246 |
| 2017/0213438 A1* | 7/2017 | Peng | A61B 5/08 |
| 2017/0238842 A1* | 8/2017 | Jacquel | A61B 5/743 |
| 2019/0029604 A1* | 1/2019 | Jones | A61B 5/0816 |

* cited by examiner

160

| Motion Frequency 243 |
| --- |
| Motion Magnitude 245 |
| Motion Duration 247 |
| Sleep Length 249 |
| Sleep Quality 251 |
| Sleep Intervals 253 |

| Field-of-View Policy |
| :---: |
| 261 |
| Event Time Interval |
| 263 |
| Breathing Event |
| 265 |
| Large-Scale Motion |
| 267 |

FIG. 1D

GENERATING A BREATHING ALERT

CROSS-REFERENCE TO RELATED APPLICATIONS

This application claims priority to U.S. Provisional Patent Application No. 62/383,769 entitled "IDENTIFYING A BREATHING EVENT" and filed on Sep. 6, 2016 for Jacob Gunther, which is incorporated by reference.

BACKGROUND

Field

The subject matter disclosed herein relates to breathing and more particularly relates to identifying an alert.

Description of the Related Art

It is often desirable to determine if a person is breathing.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which:

FIG. 1D is a schematic block diagram illustrating one embodiment of breathing data;

DETAILED DESCRIPTION OF THE INVENTION

Figure 1A:
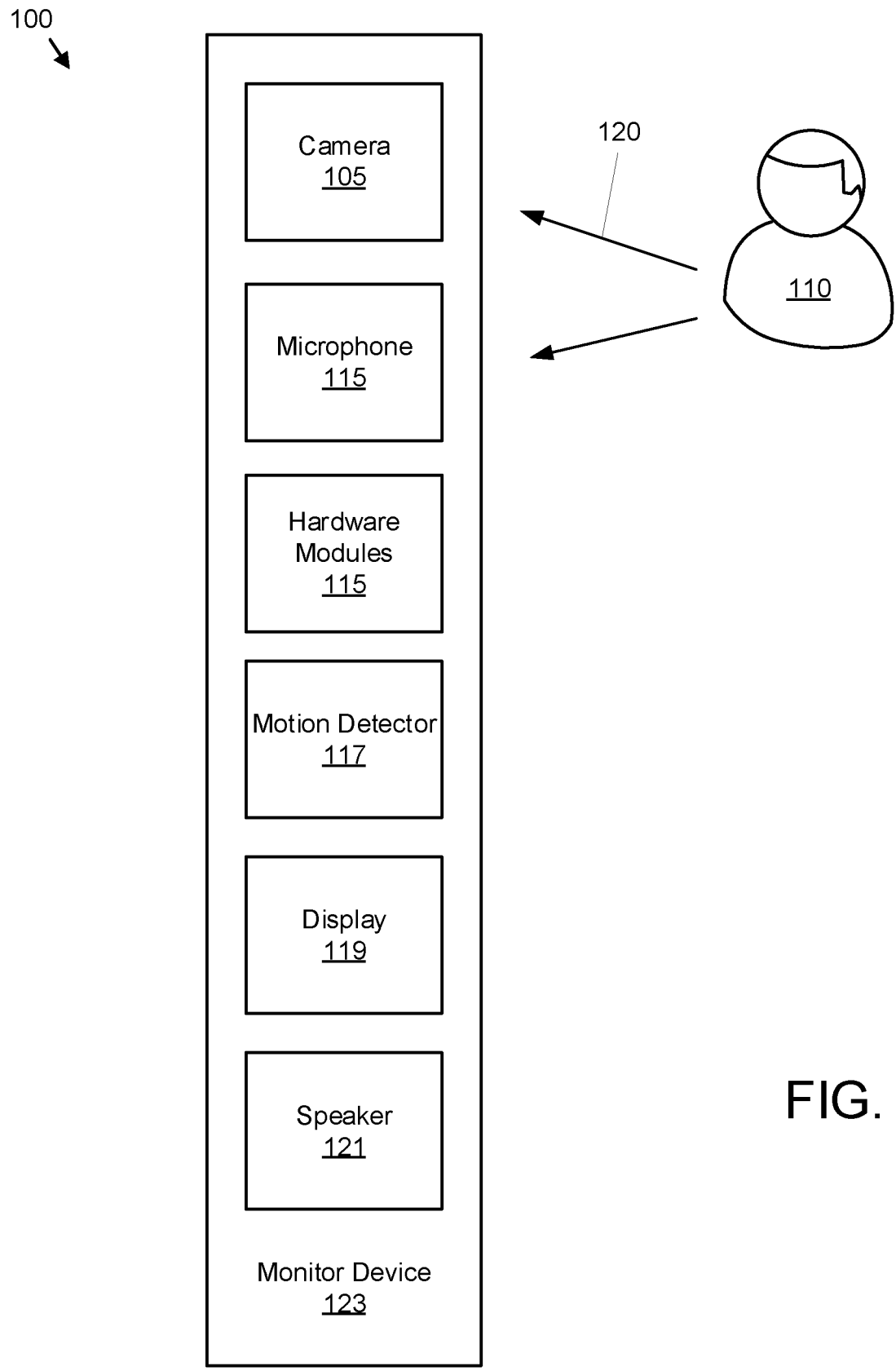
FIG. 1A is a schematic block diagram illustrating one embodiment of a breathing event identification system.

As will be appreciated by one skilled in the art, aspects of the embodiments may be embodied as a system, method or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages, including an object-oriented programming language such as Python, Ruby, Java, Smalltalk, C++ or the like and conventional procedural programming languages, such as the "C" programming language or similar programming languages, and/or hardware definition languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. The code may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

FIG. 1A is a schematic block diagram illustrating one embodiment of a breathing event identification system 100.

The system 100 may identify a breathing event and/or large-scale motion for a subject 110 from a video stream of the subject 110 captured by a camera 105. In addition, the system 100 may generate an alert if no breathing event is identified and no large-scale motion is identified. In one embodiment, the system 100 also includes a monitor device 123. The monitor device 123 may include the camera 105, microphone 115, hardware modules 115, and a motion detector 117. In addition, the monitor device 123 may include a display 119 and/or a speaker 121. In one embodiment, the hardware modules 115 comprise dedicated semiconductor circuits. The dedicated semiconductor circuits may include a memory. In addition, the hardware modules 115 may comprise a computer.

The camera 105 may capture a video stream 120 of the subject 110. The camera 105 may employ a bandpass filter in the range of 0.8-2.5 micrometers. In addition, the camera 105 may employ Charge Coupled Device (CCD) that is tuned to 1.5 micrometers. The camera 105 may capture the video stream as infrared image frames.

When a subject 110 may be at risk for ceasing to breathe, it is advantageous to monitor the subject 110 and identify the breathing rate and/or detect the cessation of breathing so that timely aid may be given. It is further advantageous to employ noninvasive monitoring to identify breathing events so the subject 110 is not disturbed.

Breathing events may be detected optically and audibly. For example, baby monitors may be used to monitor a baby's breathing through a video (sequence of images) of the baby captured by a camera 105 and/or a sound of the baby's breathing captured by the microphone 115. Unfortunately, when identifying breathing events, the consequences of both false positives and false negatives is so high that monitoring must detect breathing events with extreme accuracy.

The embodiments described herein identify breathing events and/or large-scale motions based on a video stream as will be described hereafter. The embodiments further generate alerts, present displays, and present statistics based on the breathing events.

Figure 1B:
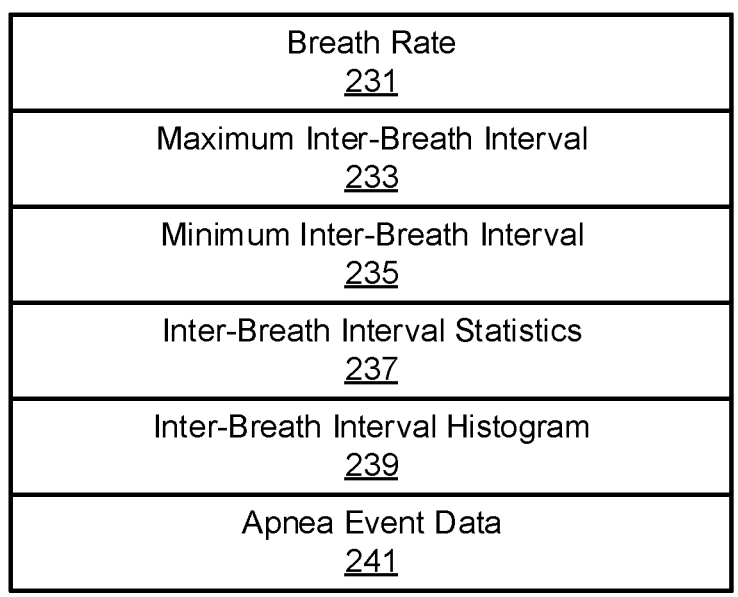
FIG. 1B is a schematic block diagram illustrating one embodiment of a breathing report.

FIG. 1B is a schematic block diagram illustrating one embodiment of a breathing report 165. The breathing report 165 may be organized as a data structure in a memory. In the depicted embodiment, the breathing report 165 includes a breath rate 231, a maximum inter-breath interval 233, a minimum inter-breath interval 235, inter-breath interval statistics 237, an inter-breath interval histogram 239, and apnea event data 241.

The breath rate 231 may represent a frequency of breathing. The maximum inter-breath interval 233 may specify a longest interval between breathing events. The minimum inter-breath interval 235 may specify a shortest interval between breathing events. The inter-breath interval statistics 237 may specify one or more of a mean, average, and mode of intervals between breathing events. The inter-breath interval histogram 239 may describe the relative frequencies of breath intervals between breathing events. The breath intervals may be organized into one or more ranges.

The apnea event data 241 may be calculated from the breath rate 231, maximum inter-breath interval 233, minimum inter-breath interval 235, inter-breath interval statistics 237, and inter-breath interval histogram 239. The apnea event data 241 may be used to identify sleep apnea events.

Figure 1C:
FIG. 1C is a schematic block diagram illustrating one embodiment of a motion report 160.

FIG. 1C is a schematic block diagram illustrating one embodiment of a motion report 160. The motion report 160 maybe organized as a data structure in a memory. In the depicted embodiment, the motion report 160 includes a motion frequency 243, a motion magnitude 245, a motion duration 247, a sleep length 249, a sleep quality 251, and sleep intervals 253.

The motion frequency 243 may describe the frequency of large-scale motions by the subject 110. The motion magnitude 245 may describe a number of pixels affected by each motion. The motion duration 247 may describe the duration from start to end of each large-scale motion by the subject 110.

The sleep length 249 may describe a length of a time interval during which the subject 110 is asleep. The sleep quality 251 may estimate the restfulness of the sleep for the subject 110. The sleep intervals 253 may describe each interval during which the subject 110 is quietly asleep.

FIG. 1D is a schematic block diagram illustrating one embodiment of breathing data. The breathing data maybe organized as a data structure in a memory. In the depicted embodiment, the breathing data includes a field of view policy 261, an event time interval 263, a breathing event 265, and a large-scale motion 267.

The field of view policy 261 may specify when the subject 110 can be satisfactorily viewed by the camera 105. The event time interval 263 may specify a time interval during which a breathing event 265 or a large-scale motion 267 of the subject 110 must be identified in order to not generate an alert. The breathing event 265 may be an identified breath by the subject 110. The large-scale motion 267 may indicate motion by the subject 110. The motion may make determining a breathing event 265 impossible.

Figure 2A:
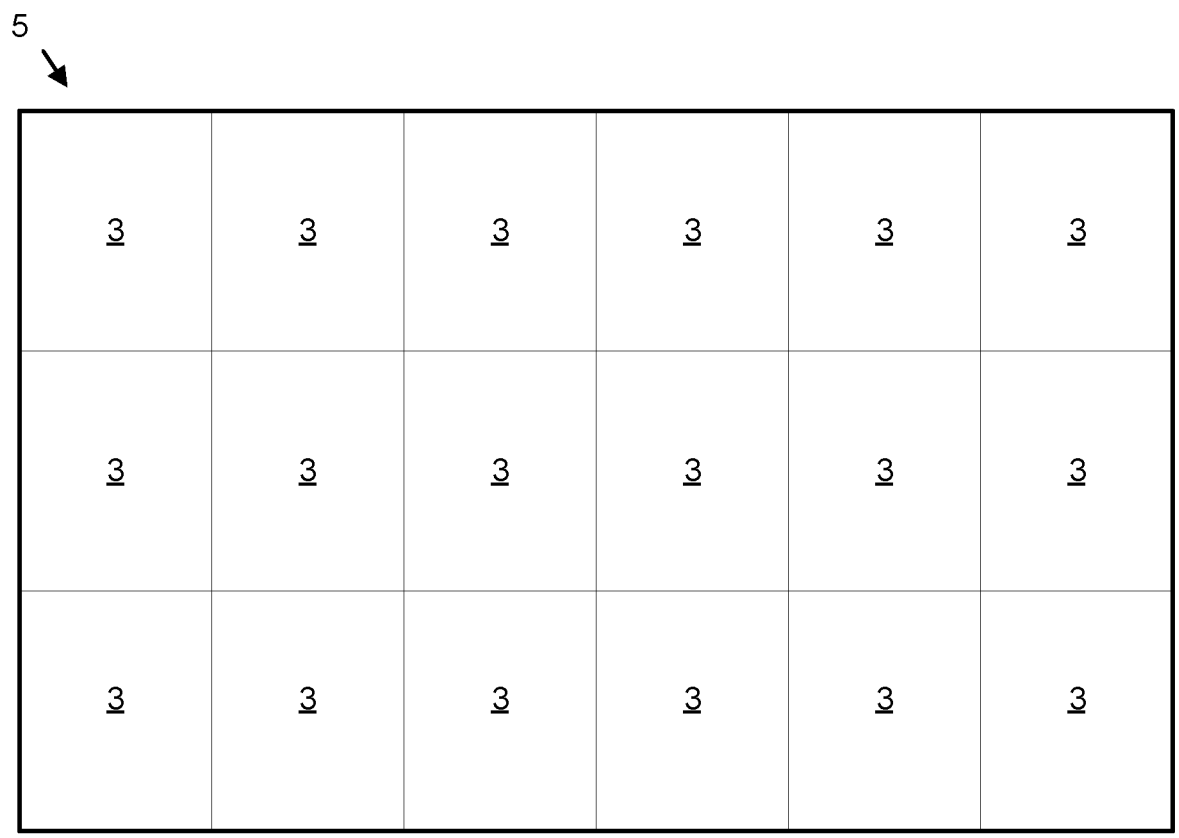
FIG. 2A is a schematic diagram illustration one embodiment of regions in an image frame.

FIG. 2A is a schematic diagram illustration one embodiment of regions 3 in an image frame 5. In the depicted embodiment, and an image frame 5 is divided into a rectangular grid of one or more regions 3. In this embodiment, all regions 3 have rectangular shapes and are equal in size.

Figure 2B:
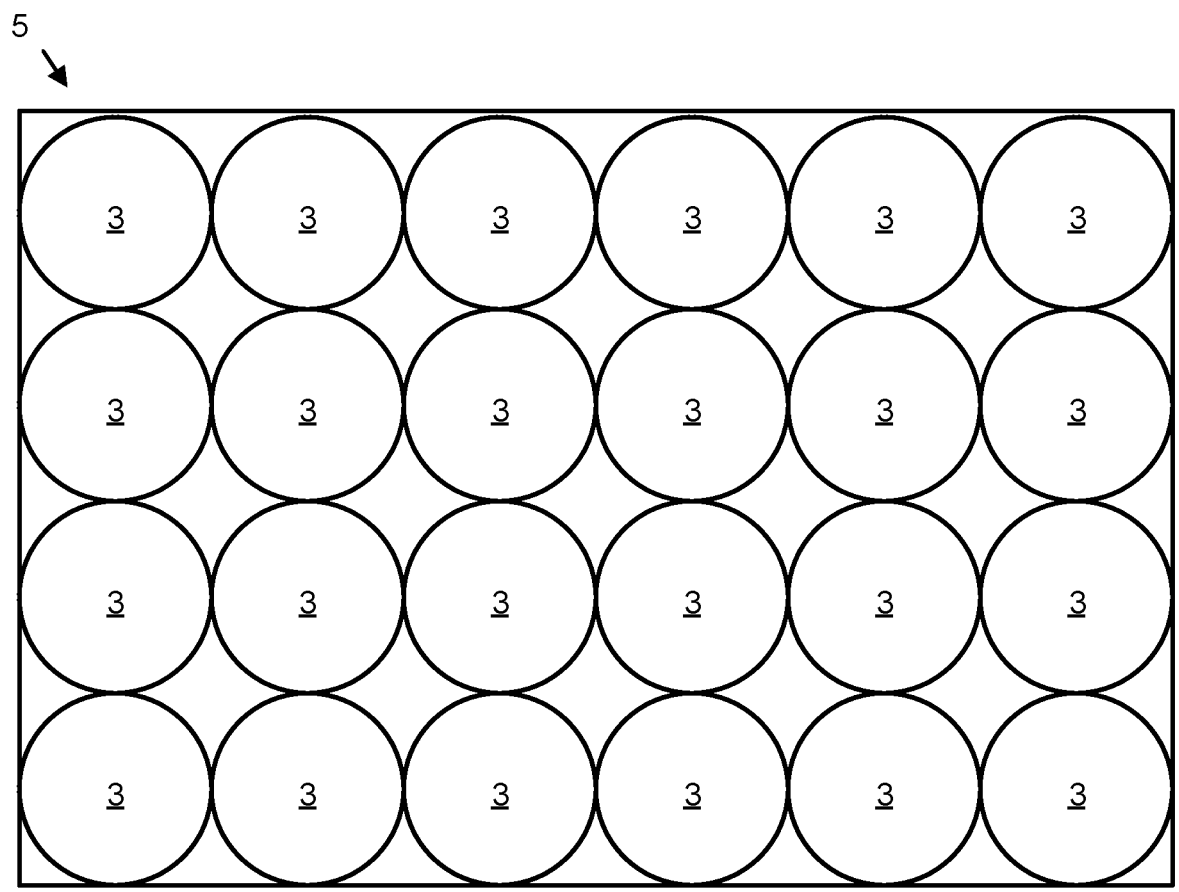
FIG. 2B is a schematic diagram illustration one alternate embodiment of regions in an image frame.

FIG. 2B is a schematic diagram illustration one alternate embodiment of regions 3 in an image frame 5. In the depicted embodiment, an image frame 5 is divided into circular shaped regions 3. The regions 3 do not overlap and some pixels of the image frame 5 are not included in any region 3.

Figure 2C:
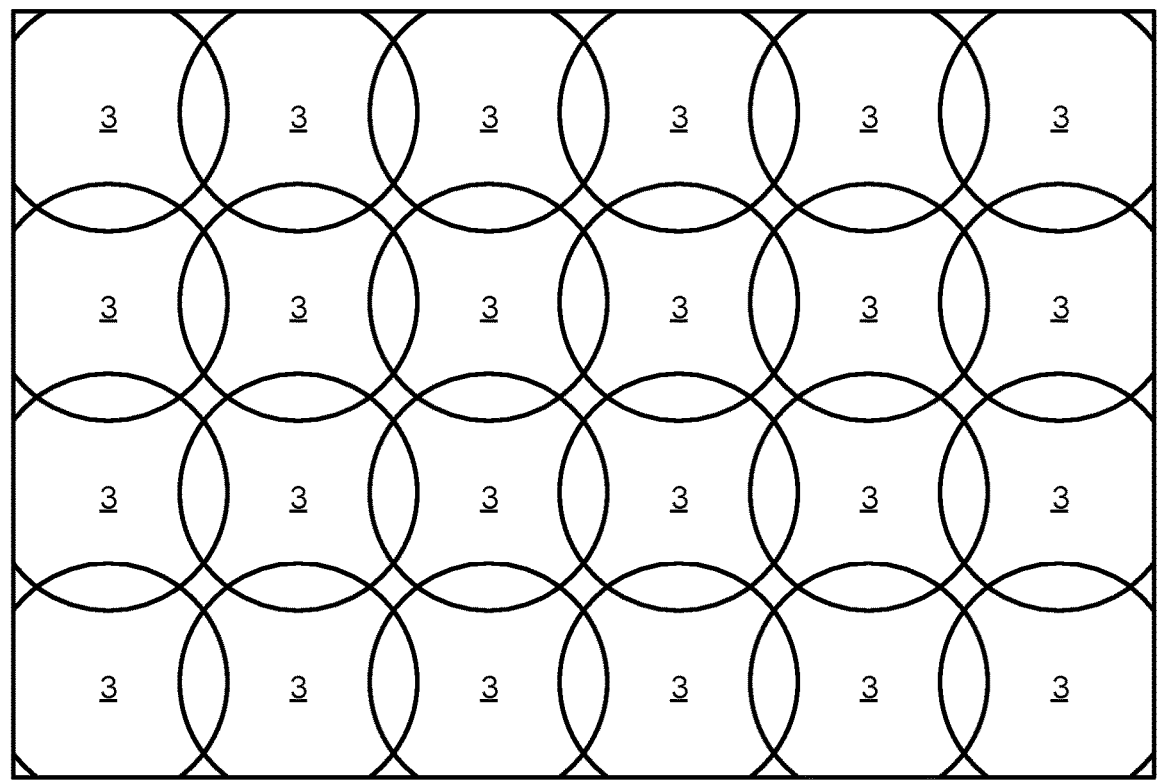
FIG. 2C is a schematic diagram illustration one alternate embodiment of regions in an image frame.

FIG. 2C is a schematic diagram illustration one alternate embodiment of regions 3 in an image frame 5. In the depicted embodiment, the image frame 5 is divided into circular shaped regions 3. The regions 3 overlap so that some pixels of the image frame 5 are included in two or more regions 3 while other pixels are not included in any region 3.

Figure 2D:
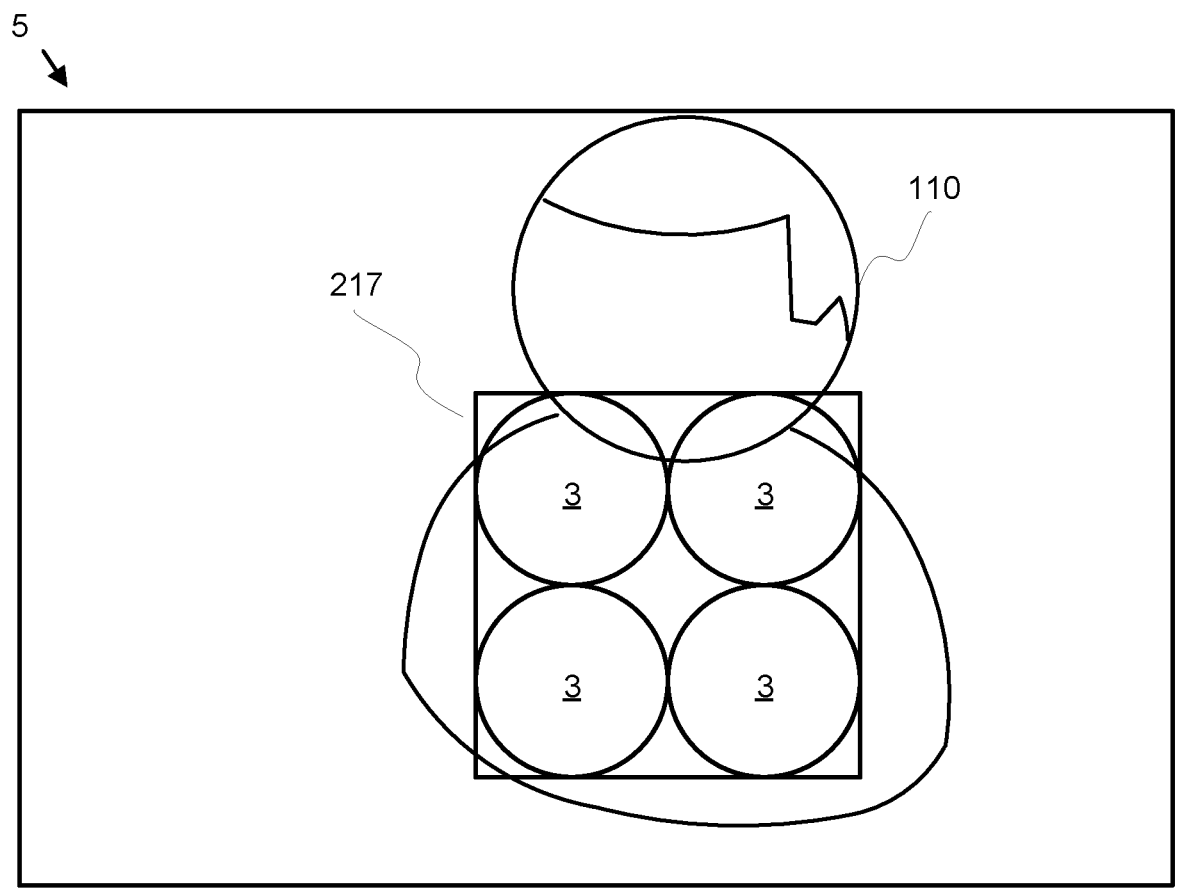
FIG. 2D is a schematic diagram illustration one embodiment of user selected regions in an image frame.

FIG. 2D is a schematic diagram illustration one embodiment of user selected regions 3 in an image frame 5. Using an interface, a user may identify the pixels in the image frame 5 that are occupied by the subject 110 with user input defining a user selected area 217. When user input is provided, the regions 3 could be obtained by dividing the user selected area 217.

Figure 2E:
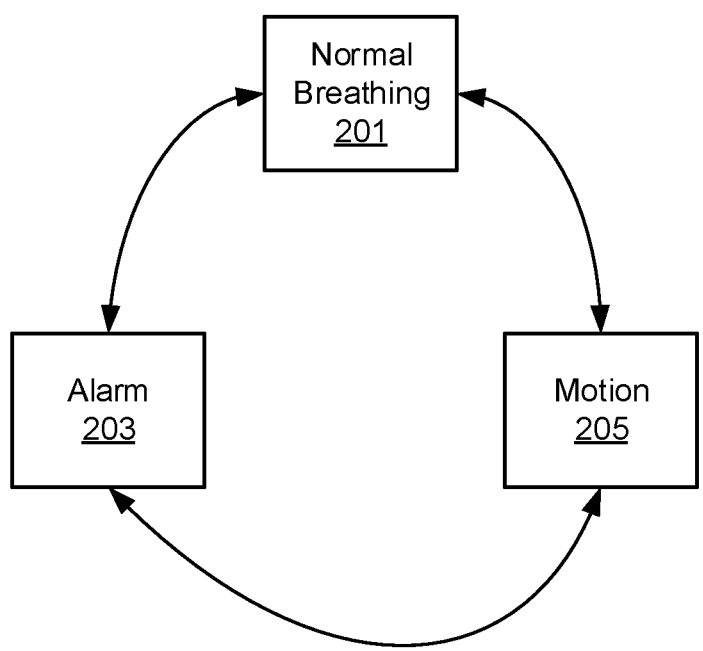
FIG. 2E is a schematic block diagram illustrating one embodiment of breathing event identification states.

FIG. 2E is a schematic block diagram illustrating one embodiment of breathing event identification states. The depicted embodiment includes a normal breathing state 201, an alarm state 203, and a motion state 205 of a state machine. When normal breathing is detected by the monitor device 123 in either the alarm state 203 where the motion state 205, the state machine transitions to the normal breathing state 201. Normal breathing may be indicated by a breath event 265 within the event time interval 263. When large-scale motion 267 is detected by the monitor device 123 in either the alarm state 203 or the normal breathing state 201, the state machine transitions to the motion state 205. In one embodiment, the large-scale motion 267 is detected within the event time interval 263. If normal breathing and motion are not detected by the monitor device 123 in either the normal breathing state 201 or the motion state 205, the state machine transitions to the alarm state 203. In one embodiment, the normal breathing and/or large-scale motion 267 must be detected within the event time interval 263 or the state machine transitions to the alarm state 203. The use of breathing event identification states is described in more detail in FIG. 3A.

Figure 3A:
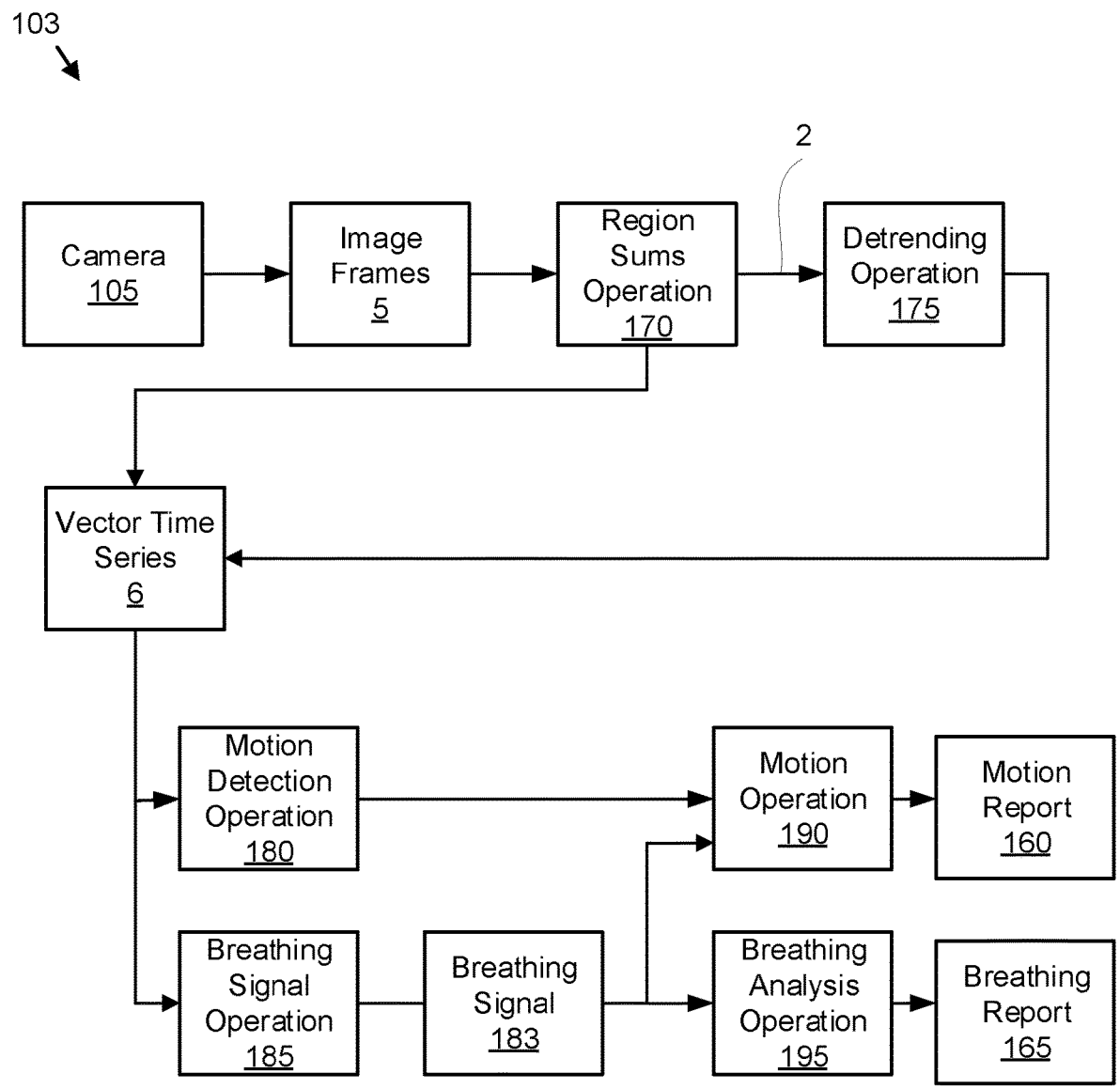
FIG. 3A is a schematic block diagram illustrating one embodiment of a breathing event identification process.

FIG. 3A is a schematic block diagram illustrating one embodiment of a breathing event identification process 103. The video stream 120 of a subject comprising image frames 5 are captured by a camera 105. The camera 105 outputs image frames 5. Image frames 5 can be produced in many different formats including color images with red, green, and blue color channels, grayscale images, infrared images, depth images. Some formats may be derived from others. For example, grayscale image frames 5 may be computed from red, green, blue images.

A sequence of operations may be applied to extract a breathing signal 183. The order in which the operations are performed may vary. A region sums operation 170 computes region sums 2. The region sums operation 170 adds together all the pixels intensities lying in a region 3 of the image frame 5. The regions 3 may take different shapes. For example, the image frame 5 may be divided into a rectangular grid of regions as shown in FIG. 2A. The regions could be circularly shaped as illustrated in FIG. 2B-D. The regions could be vertical or horizontal lines across the image. Other contours besides straight lines could also be used. The regions may be overlapping as illustrated in FIG. 2C or non-overlapping as illustrated in FIG. 2B. Not every pixel in the image frame 5 need be included in a region as illustrated in FIGS. 2B-C.

The selection of regions 3 could be guided by input from a user through a graphical user interface as illustrated in FIG. 2D. Once region selection with the user input is performed, the regions 3 may be held fixed during the remainder of the processing. In one embodiment, computing the region sums 2 is not required. In some embodiments, subsequent operations may be performed directly on the pixel intensities.

In one embodiment, the output of the region sums operation 170 is a vector time series 6 in which there is one element in the vector for each region. When region sums 2 are not computed, the vector contains one element for each pixel in the image frame.

Figure 3B:
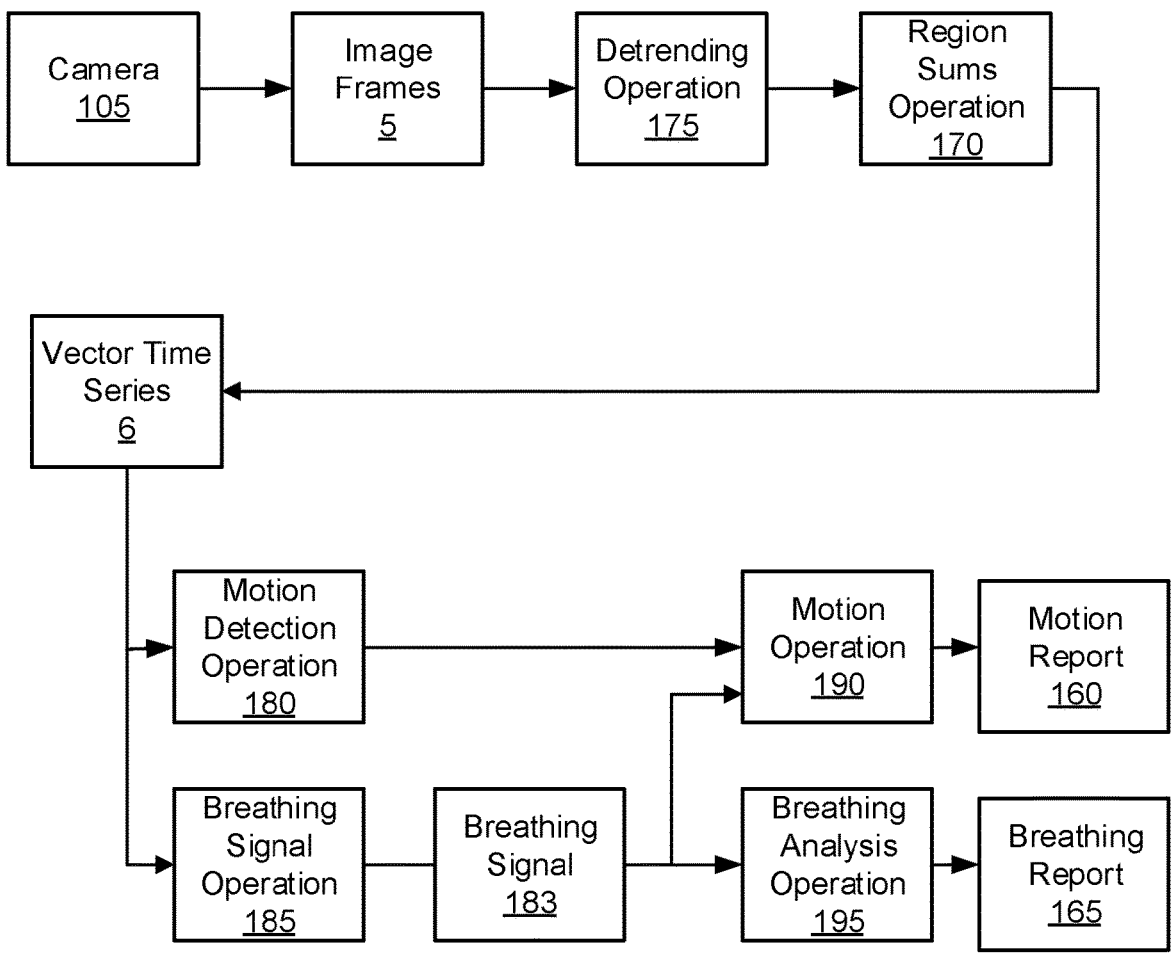
FIG. 3B is a schematic block diagram illustrating one alternate embodiment of a breathing event identification process.

In the depicted embodiment, the detrending operation 175 is applied after computing the region sums 2. However, the region sums operation 170 and the detrending operation 175 may be performed in the opposite order as shown in FIG. 3B. The detrending operation 175 removes a signal mean in a region 3. The detrending operation 147 may also normalize an amplitude of the signal for the region 3. Whereas, the region sums operation 170 combines pixels spatially across one image frame 5, the detrending operation 175 operates on a signal in the temporal dimension. The detrending operation 175 is not required. In one embodiment, the detrending operation 175 is not performed. The dimension of the vector time series 6 output by the detrending operation 175 is the same as its input to the detrending operation 175.

The breathing signal operation 185 may estimate the breathing signal 183. In one embodiment, a sparse plus low-rank decomposition is used as illustrated hereafter in FIG. 3C. In an alternate embodiment, the breathing signal operation 185 uses subspace tracking. Breathing leads to small variations in pixel intensities that are concentrated in areas of the image frame 5 that are unknown a priori. Breathing manifests itself as quasiperiodic variations in certain region sums 2. Not all region sums 2 are affected by breathing. In regions where it is present, the phase of the breathing signal 183 may be exactly opposite of the phase of the breathing signal 183 in other regions. The breathing signal operation 185 may automatically combine the region sums 2 that exhibit breathing and neglect those regions sums 2 that do not exhibit breathing. This automatic breathing signal operation 185 may also account for the phase of the breathing signal 183 in regions 3 where breathing is present.

One process for combining the region sums 2 is to use a linear combination. The coefficients in the linear combination may be set to include regions 3 where breathing is present and exclude regions 3 where breathing is absent. When a coefficient is set to zero, the corresponding region sum 2 is not included in the final estimate of the breathing signal. When a coefficient is nonzero, the corresponding region sum 2 is included in the linear combination. The algebraic sign of the coefficient (positive or negative) may be used to coherently combine region sums 2 and accounts for the phase of the breathing signal 183 in each region sum 2. The weights and/or coefficients in a linear combination of the region sums 2 may be automatically selected to include regions 3 where breathing is present and exclude regions 3 where breathing is absent. The resulting linear combination is a scalar-valued time series which is the final breathing signal 183. Subspace tracking may be used to automatically adjust the coefficients in the linear combination. In one embodiment, singular value decomposition is used for the subspace tracking.

In an alternate embodiment, an adaptive subspace algorithm such as a Projection Approximation Subspace Tracking (PAST) that is adapted to image processing may be used. The adaptive subspace algorithm may adaptively update estimates of an orthonormal basis for pixel vector space spanned by the incoming pixel vectors. The dominant basis vector learned by the adaptive subspace algorithm may be used as the coefficients in the linear combination. In addition, one of the steps in the adaptive subspace algorithm is to compute the linear combination. Thus, the adaptive subspace algorithm computes an estimate of the breathing signal 183.

The adaptive subspace algorithm may be applied to the vector of region sums 2. It may also be applied to the raw pixels in the original image frame 5. The adaptive subspace algorithm may also be applied to the video stream of moving objects obtained from a sparse plus low-rank decomposition. Alternative algorithms for subspace tracking and subspace updating may also be used.

After the breathing signal 183 is estimated, then a breathing analysis operation 195 is performed and a breathing report 165 is produced. The breathing report 165 may include a variety of information, including a current breath rate 231. The breath rate 231 may be saved over a period of time in the breathing report 165 so that breathing history may be analyzed and reported. Breathing variability may also be reported. Irregular breathing and breathing anomalies may be of interest. Breathing analysis may include the minimum inter-breath interval 233 and maximum inter-breath interval 235 and the inter-breath interval statistics 237 such as mean, median, mode, standard deviation, etc. The inter-breath interval histogram 239 may be computed. Apnea events could be counted and time-stamped as the Apnea event data 241.

The motion operation 190 may generate the motion report 160. The motion operation 190 may employ the breathing event identification states of FIG. 2E. Breathing can only be accurately measured when the subject is relatively still. When, for example, a sleeping infant rolls over in the crib, the large-scale motion 267 causes large intensity changes in image pixels that lead to large region sum values. This masks the breathing signal 183. Therefore, large-scale motion 267 may be detected. If the subject's breathing stops, a caregiver would want to be alerted in order to respond and resuscitate the child. Information about motion is contained in the region sums 2. Motion may be detected using a classic hypothesis test. The null hypothesis is that no motion is present. The alternative is that motion is present. Motion causes a significant rise in the variance of region sums, detecting the motion. Classic detection methods may be applied. Modern machine learning techniques can also be applied.

Absence of both large-scale motion 267 and breathing events 265 indicates that an alert should be generated. The region sums 2 can be analyzed to detect when all motion and breathing stop. The estimated breathing signal 183 provides additional information. The region sums 2 and breathing signal 183 are fed into a motion operation 190. The motion operation 190 may employ the breathing event identification states of FIG. 2E. Transitions between the normal breathing state 201 and the motion state 205 are detected by the hardware modules 115. The alarm state 203 is entered when all large-scale motion 267 goes to zero and when the breathing signal 183 drops below a prescribed level and/or no breathing events 265 are detected.

A motion report 160 may be generated and provide information to a user. Motion and breathing information can be used to evaluate the sleep length 249 and the sleep quality 251. The onset and ending of sleep intervals 253 be timestamped.

FIG. 3B is a schematic block diagram illustrating one alternate embodiment of a breathing event identification process 103. The process 103 of FIG. 3A is shown with the detrending operation 175 performed before the region sums operation 170.

Figure 3C:
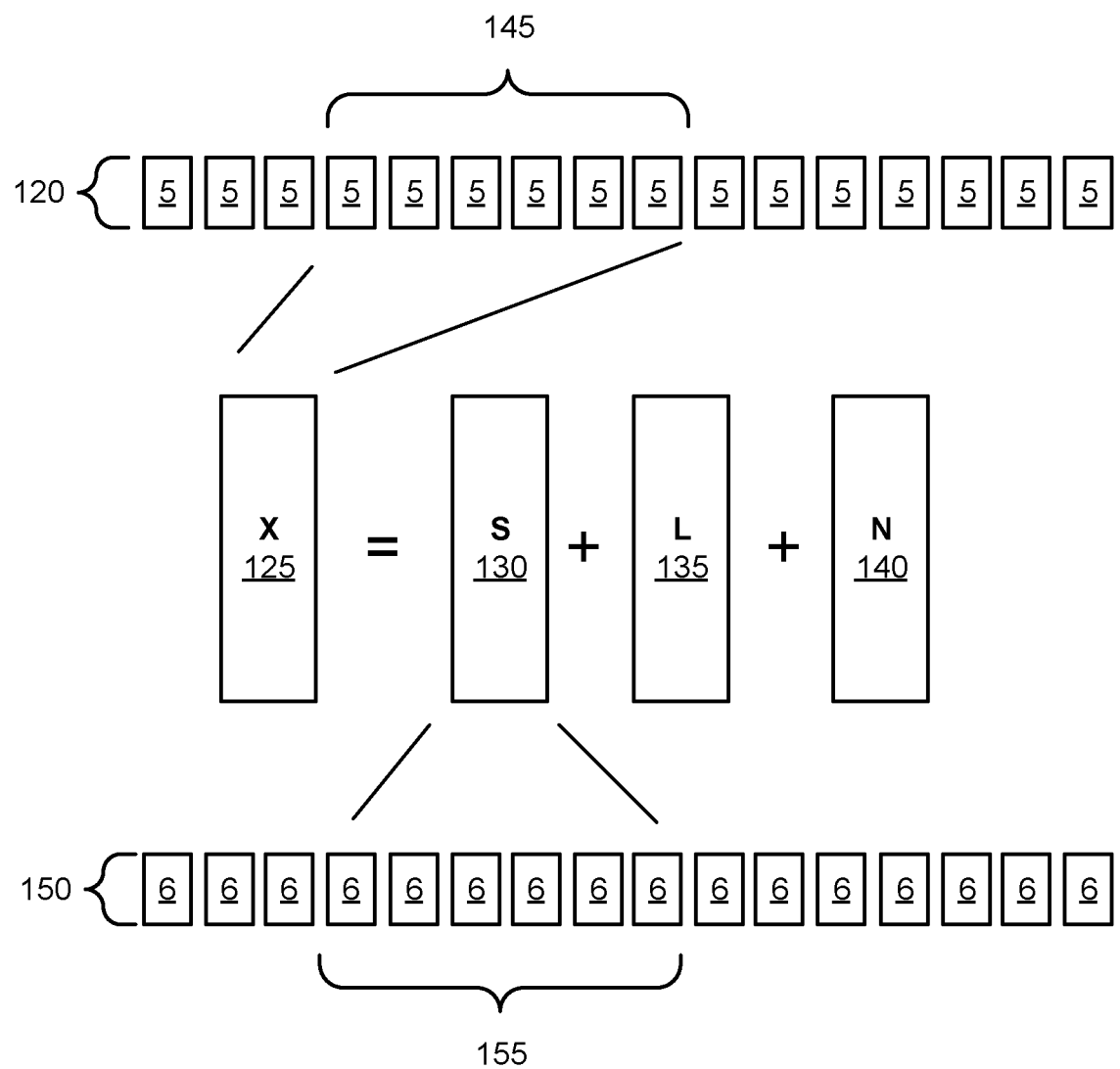
FIG. 3C is a schematic diagram illustrating one embodiment of a video stream of moving objects generation process.

FIG. 3C is a schematic diagram illustrating one embodiment of a video stream of moving objects generation process 101. The process 101 generates a video stream of moving objects 150 from a video stream 120 comprising image frames 5 of the subject 110. The process 101 receives the video stream 120 from the camera 105. The video stream 120 comprises a sequence of image frames I(t) 5 that are indexed by a cursor t. In addition, the video stream 120 may include one or more channels that may include but are not limited to an optical color image channel such as a Red Green Blue (RGB) channel, a grayscale image channel, and an infrared image channel.

The process 101 may define a window length N. The process may further extract a windowed video subsequence 145 from the video stream 120 as the sequence I(t−N+1), I(t−N+2), I(t−N+3), . . . , I(t−2), I(t−1), I(t). The process 101 may organize the windowed video sequence into a matrix X 125. In one embodiment, X 125 is an M by N matrix, and may include M rows and N columns.

In one embodiment, M is calculated as a product of a height of an image frame 5 of the video stream 120 in pixels, a width of the image frame 5 of the video stream 120 in pixels, and a number of channels in the image frames of the video stream 120. As a result, the matrix X 125 may be organized as a plurality of vectors with a vector for each image frame I in the windowed video sequence 145. The organization of the matrix X 125 greatly simplifies and enhances the calculation of the breathing event 265.

The process 101 may decompose the matrix X 125 into a sparse matrix S 130 representing moving objects and a low rank matrix L 135 representing non-moving objects as will be described hereafter. In one embodiment, the decomposition of matrix X 125 includes an additive noise matrix N 140.

The process 101 reconstructs the video stream of moving objects 150 from the sparse matrix S 130. In one embodiment, each pixel of the reconstructed video stream of moving objects 150 comprises a scaler time series. Alternatively, each pixel of the reconstructed video stream of moving objects 150 includes a vector time series. In one embodiment, a sliding sparse subsequence 155 that corresponds to the windowed video sequence 145 is extracted from the video stream of moving objects 150.

Figure 4A:
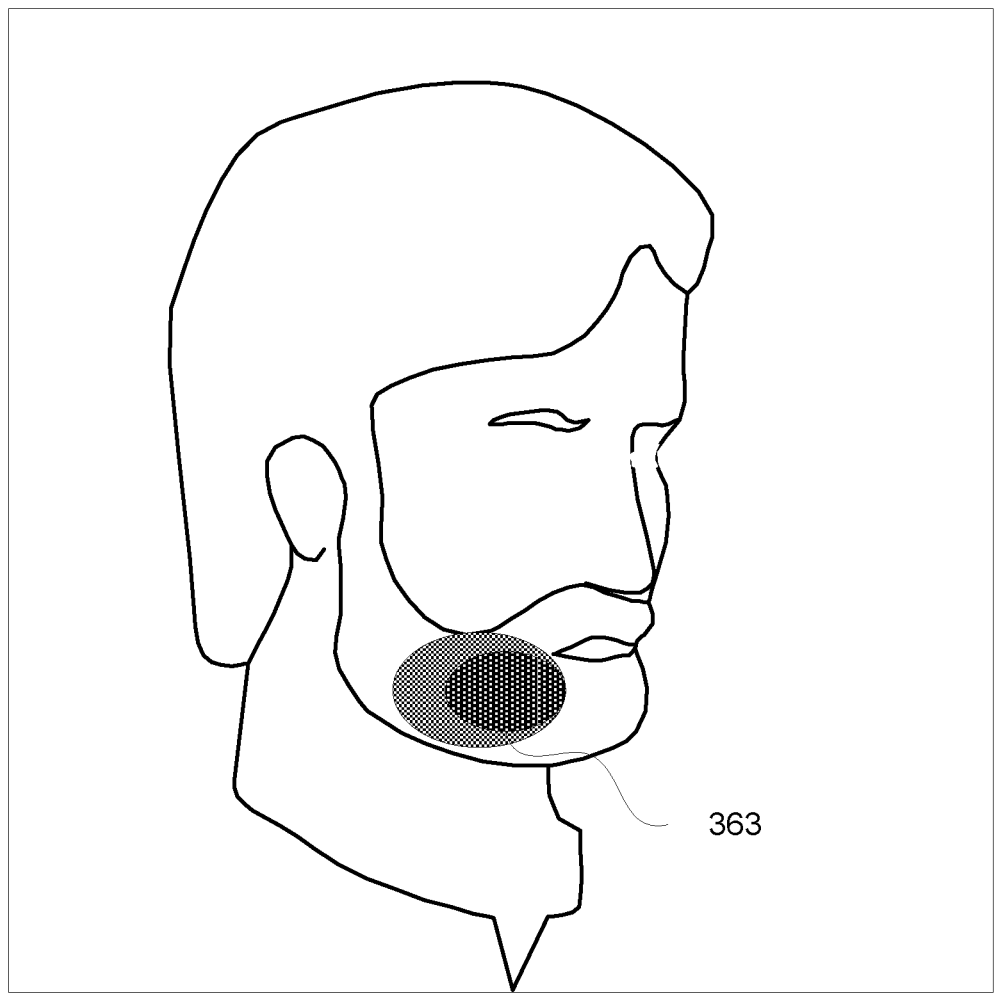
FIG. 4A is a drawing illustrating one embodiment of a heat map.

FIG. 4A is a drawing illustrating one embodiment of a heat map 363. In the depicted embodiment, a video stream 120 of the subject 110 is shown with the heat map 363 superimposed on the video stream 120. In one embodiment, the breath rate 231 from a plurality of breathing events 265 is encoded as the heat map 363. The heat map 363 may be overlaid on the video stream 120 for display to a user.

Figure 4B:
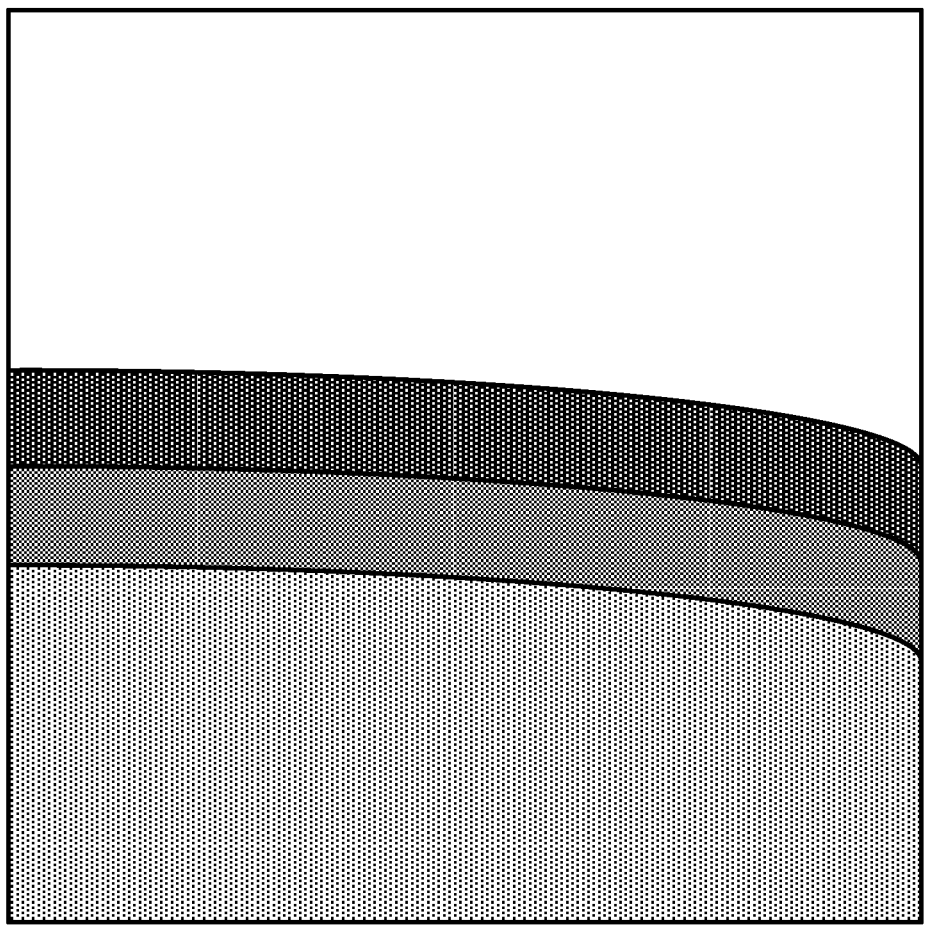
FIG. 4B is a drawing illustrating one alternate embodiment of a heat map.

FIG. 4B is a drawing illustrating one alternate embodiment of a heat map 363. In the depicted embodiment, a video stream 120 of the subject 110 such as the chest region of the subject 110 is shown with a heat map 363 superimposed on the video stream 120. The heat map 363 may be encoded with the large-scale motion 267 of the subject 110. In one embodiment, the heat map 363 encodes the motion magnitude 245 of the subject 110.

Figure 4C:
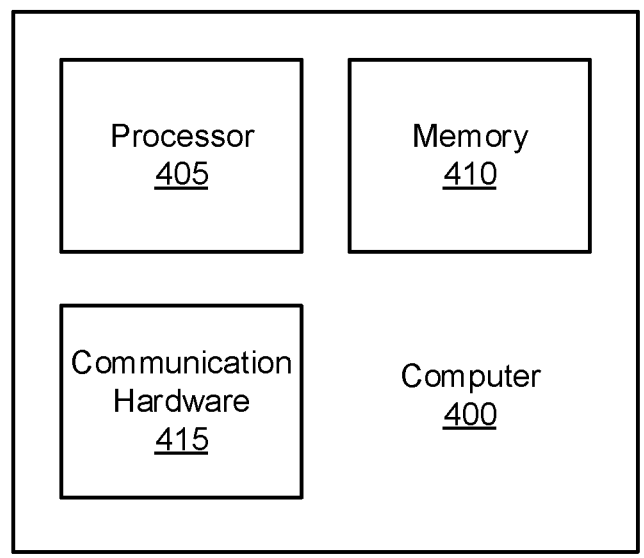
FIG. 4C is a schematic block diagram illustrating one embodiment of the computer.

FIG. 4C is a schematic block diagram illustrating one embodiment of the computer 400. The computer 400 may be embodied in the hardware modules 115. In the depicted embodiment, the computer includes a processor 405, a memory 410, and communication hardware 415. The memory 410 may include a semiconductor storage device. The memory 410 may store code. The processor 405 may execute the code. The communication hardware 415 may communicate with other elements of the monitor device 123 and/or other devices such as a mobile telephone network or a Wi-Fi network.

Figure 4D:
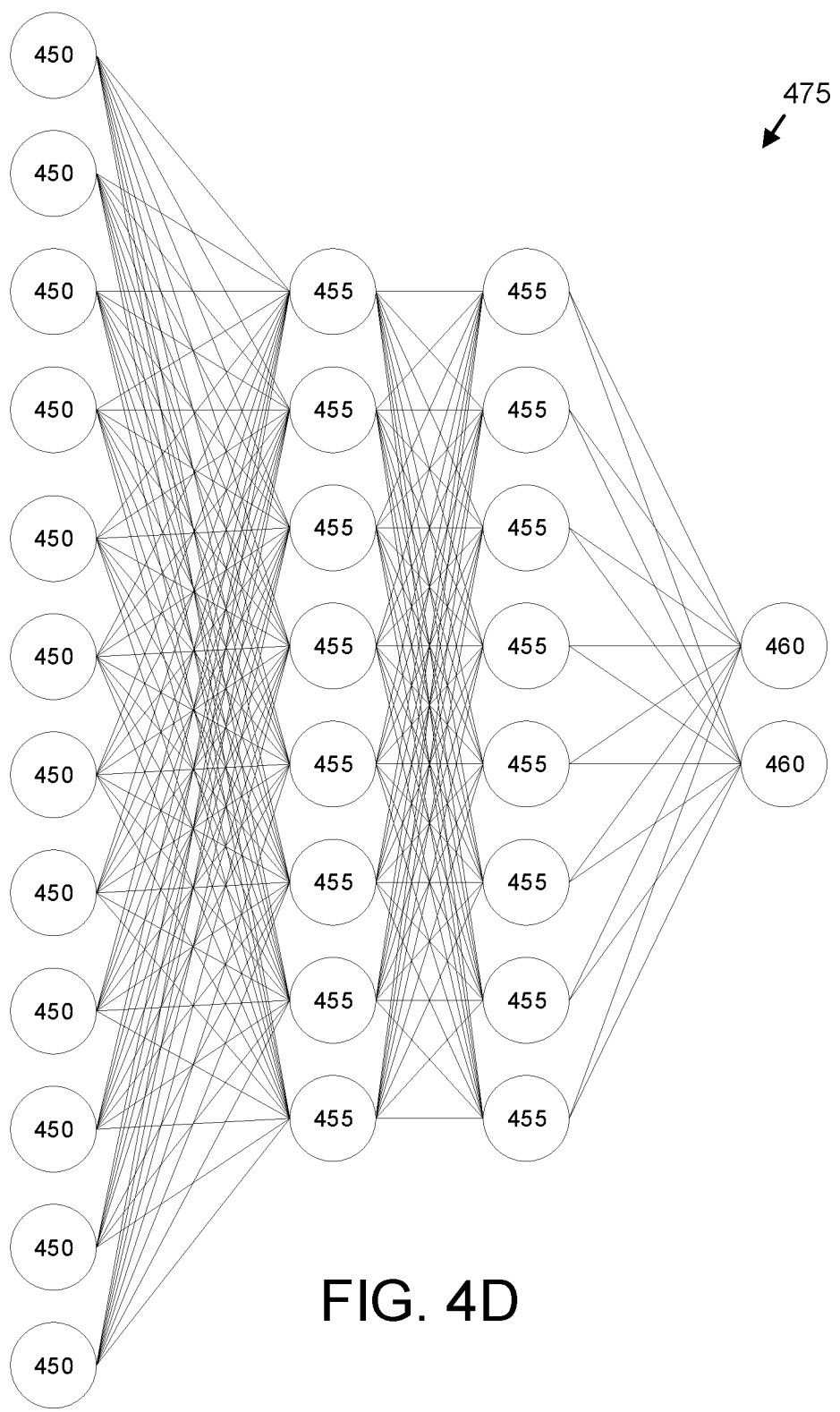
FIG. 4D is a schematic block diagram illustrating one embodiment of a neural network.

FIG. 4D is a schematic block diagram illustrating one embodiment of a neural network 475. In the depicted embodiment, the neural network 475 includes one or more hidden neurons 455. The hidden neurons 455 receive inputs from one or more input neurons 450 and communicate with one or more output neurons 460. The output neurons 460 may indicate predictions such as breathing normally and/or moving. The neural network 475 may be trained with one or more video streams 120 and one or more motion reports 160 and/or breathing reports 165 corresponding to the one or more video streams 120. In addition, a live video stream 120 may be presented to the input neurons 450 of the trained neural network 475 and the output neurons 460 may generate a current motion report 160 and/or a current breathing report 165.

Figure 5A:
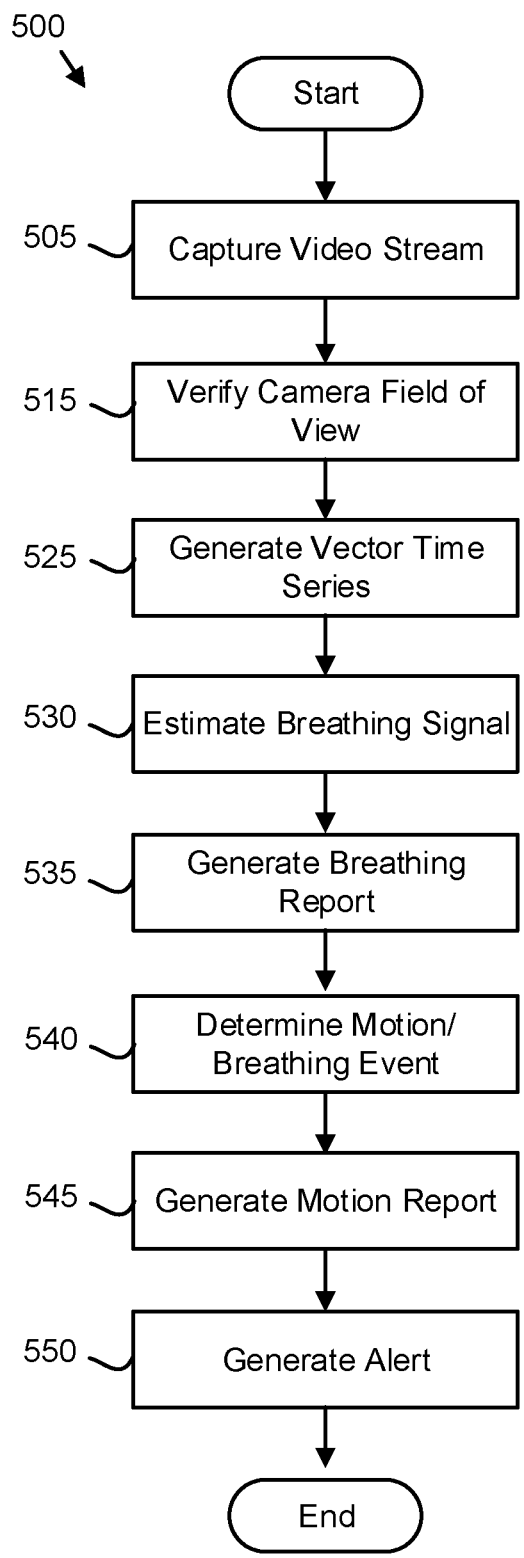
FIG. 5A is a schematic flow chart diagram illustrating one embodiment of a breathing signal estimation method.

FIG. 5A is a schematic flow chart diagram illustrating one embodiment of a breathing signal estimation method 500. The method 500 may generate the breathing report 165, the motion report 160, and/or generate an alert. The method 500 may be performed by the monitor device 123.

The method 500 starts, and in one embodiment, the camera 105 captures 505 the video stream 120 of the subject 110. The video stream 120 may be captured 505 without disturbing the subject 110. In one embodiment, the video stream 120 is captured 505 in an infrared spectrum.

The hardware modules 115 may verify 515 that the field-of-view of the camera 105 satisfies the field-of-view policy 261. In one embodiment, the field-of-view policy 261 is satisfied if the subject 110 fills at least 10% of the field of view of the camera 105. The hardware modules 515 may adjust the field-of-view of the camera 105 until the field-of-view policy 261 is satisfied.

The hardware modules 115 may generate 525 the vector time series 6 for the video stream 120. The time vector series 6 may comprise a vector for each image frame 5 of the video stream 120. The hardware modules 115 may divide each image frame 5 into regions 3. In addition, the hardware modules 115 may sum the pixel values in each region 3 as a pixel sum as described for FIGS. 3A-B.

The hardware modules 115 may generate 525 the vector time series 6 by dividing each image frame 5 into regions 3 and removing a signal mean in each region 3 as described for FIGS. 3A-B. In one embodiment, the signal mean is removed from the pixel sums.

In one embodiment, the hardware modules 115 estimate 530 the breathing signal 183 from the vector time series 6. The breathing signal 183 may be estimated 530 from the reconstructed video stream as described hereafter in FIG. 5B. In addition, the breathing signal 183 may be estimated 530 by applying the adaptive subspace algorithm to each vector of the vector time series 6. The hardware modules 115 may further estimate a breathing event 265 from the breathing signal 183.

The hardware modules 115 may generate 535 the breathing report 165. The breathing report 165 may be generated 535 based on the breathing signal 183 and/or the breathing event 265.

In one embodiment, the hardware modules 115 determine 540 one of a large-scale motion 267 and a breathing event 265 of the subject 110 based on the vector time series 6 and/or the breathing signal 183. The hardware modules 115 may further generate 545 the motion report 160 based on the large-scale motion 267.

In one embodiment, the hardware modules 115 generate 550 an alert and the method 500 ends. The alert may be communicated through the speaker 121. In addition, the alert may be communicated through the display 119. Alternatively, the alert may be communicated through another device such as a mobile telephone.

In one embodiment, the alert is generated 550 if both no breathing event 265 is identified and no large-scale motion 267 of the subject 110 is identified within the event time interval 263. For example, if no breathing event 265 is identified from the breathing signal 183 during the event time interval 263 and no large-scale motion 267 of the subject 110 is identified within the event time interval 263, the breathing event identification states may transition to the alarm state 203, generating the alert.

Figure 5B:
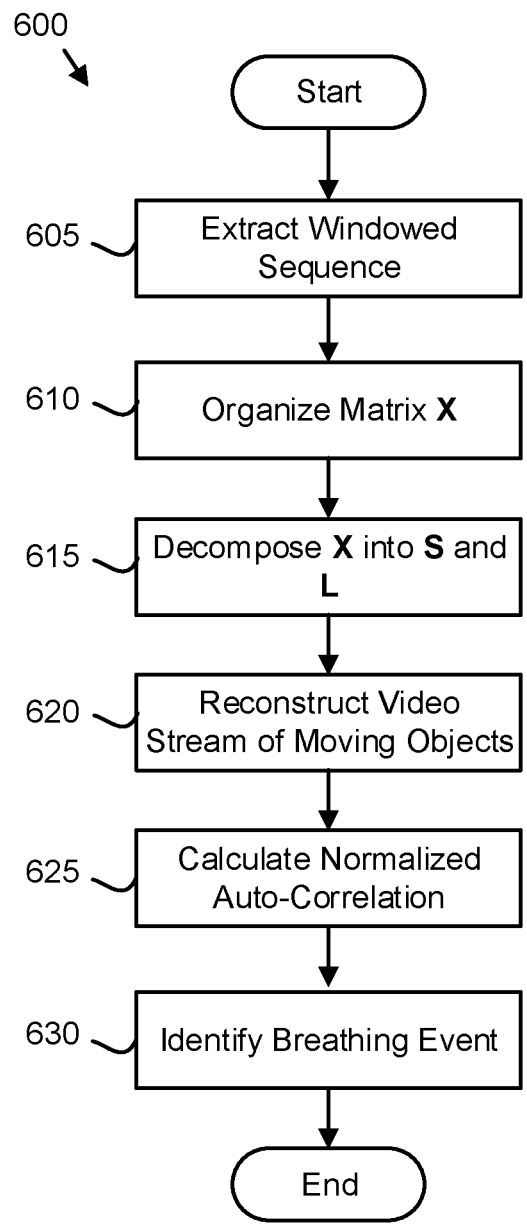
FIG. 5B is a schematic flowchart diagram illustrating one embodiment of a breathing event identification method.

FIG. 5B is a schematic flowchart diagram illustrating one embodiment of a breathing event identification method 600. The method 600 may identify a breathing event 265 from the video stream 120. The method 600 may be performed by one or more of the camera 105, the hardware modules 115, and/or the memory 420 storing code.

The method 600 starts, and in one embodiment, the hardware modules 115 extracts 605 the windowed video subsequence 145 from the video stream 120. In addition, the hardware modules 115 may organize 610 the windowed video subsequence 145 into the matrix X 125 as described in FIG. 2.

The hardware modules 115 may decompose 615 the matrix X 125 into the sparse matrix S 130 and the low rank matrix L 135. In one embodiment, the matrix X 125 is decomposed 615 using Equation 1.

$$X = S + L + N \qquad \text{Equation 1}$$

The hardware modules 115 may further initialize matrix S 130 to S=0. In addition, the hardware modules 115 may calculate the low rank matrix L 135 using Equation 2.

$$L = \text{mean}(X - S) \qquad \text{Equation 2}$$

In one embodiment, the "mean" operator returns a matrix L having the same dimensions as the input X−S in which each element on the $i^{th}$ row of L is the mean value (average value) of the corresponding row of the input X−S.

The hardware modules 115 may calculate each pixel of matrix S 130 using Equation 3, wherein $S_{\{i,j\}}$ denotes the element on the $i^{th}$ row of the matrix S and the $j^{th}$ column of the matrix S, and T is a sparsity threshold. The sparsity threshold may be set such that a specified percentage of elements in a specified matrix is populated.

$$S_{\{i,j\}} = \begin{cases} X_{\{i,j\}} - L_{\{i,j\}}, & \text{if } |X_{\{i,j\}} - L_{\{i,j\}}| < T \\ 0, & \text{otherwise} \end{cases} \qquad \text{Equation 3}$$

The hardware modules 115 may iteratively repeat the calculations of Equation 2 and Equation 3 until a stopping condition is satisfied, yielding the sparse matrix S 130.

The hardware modules 115 further reconstruct 620 the video stream of moving objects 150 from the sparse matrix S 130. In one embodiment, each column vector of the sparse matrix S 130 is reconstructed 620 as a video frame of the video stream of moving objects 150.

In one embodiment, the hardware modules 115 reconstruct 620 the video stream of moving objects 150 from a plurality of sparse matrices S 130 for a plurality of windowed video sequences 145 and the method 600 ends. The hardware modules 115 may combine corresponding vectors of each sparse matrix S 130 to reconstruct 620 the video stream of moving objects 150.

In one embodiment, the hardware modules 115 calculate 625 a normalized auto-correlation for each pixel time series of the reconstructed video stream of moving objects 150. The hardware modules 115 may identify 630 a breathing event 265 in response to an auto-correlation peak for a given pixel of the reconstructed video stream of moving objects 150 persisting over a specified number of consecutive time periods, and the method 600 ends. The time lag of the auto-correlation peak indicates the period of breathing. The reciprocal of the time lag indicates the breath rate.

The use of the reconstructed video stream of moving objects 150 greatly reduces the computational overhead of calculating the breathing signal 183. As a result, the breathing signal 183 may be calculated using limited processing power. As a result, the monitor device 123 may be fabricated at significantly reduced cost. In addition, the monitor device 123 may consume much less power, and may be powered by a battery. As a result, the utility of the monitor device 123 is significantly increased.

Figure 5C:
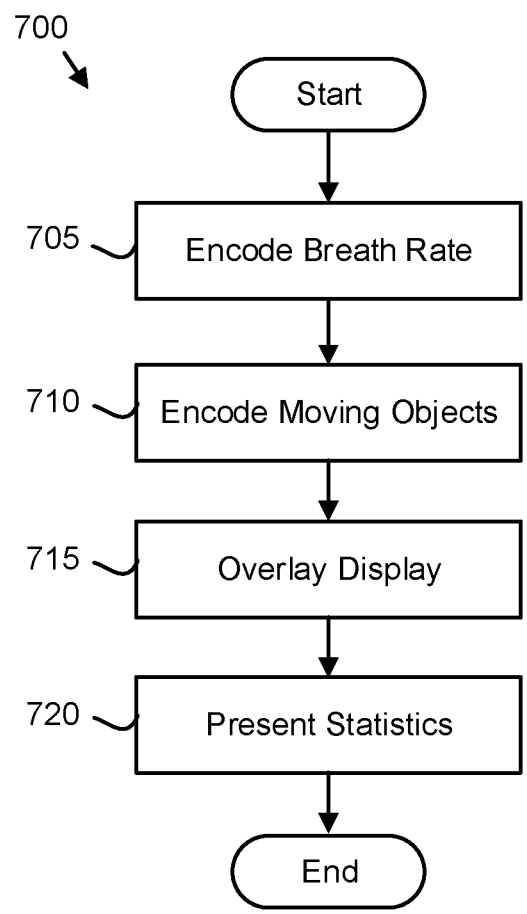
FIG. 5C is a schematic flowchart diagram illustrating one embodiment of a breathing event communication method.

FIG. 5C is a schematic flow chart diagram illustrating one embodiment of a breathing event communication method 700. The method 700 may encode and communicate information based on the breathing event. The method 700 may be performed by the monitor device 123.

The method 700 starts, and in one embodiment, the hardware modules 115 encode 705 a breath rate 231 from a plurality of breathing events. In a certain embodiment, the breath rate 231 is calculated as a function of an average time interval between each of the plurality of breathing events 265. The hardware modules 115 may further encode 705 the breath rate 231 as a heat map 363. In one embodiment, a breath rate 231 within a normal range is assigned a first heat map value and a breath rate outside of the normal range is assigned a second heat map value. Alternatively, the heat map value may be equal to a function of the breath rate 231.

The hardware modules 115 may further encode 710 the moving objects of the video stream of moving objects 150 as a heat map 363. A moving object value for each pixel may be calculated as a function of a number of corresponding pixels in a sliding sparse subsequence 155 that include moving objects. The heat map value for each pixel may be the moving object value.

The hardware modules 115 may overlay 715 the heat map 363 on the video stream 120 for display to a user. The heat map may be overlaid in a channel of the video stream 120 such as the alpha channel. For example, the alpha channel of an image frame and/or a pixel may be modified as a function of the heat map value for the image frame and/or for the pixel.

The hardware modules 115 may present 720 statistics to the user using the display 119 and the method 700 ends. The statistics may be presented 620 through the r:4 video stream 120. The statistics may include the information of the motion report 160 and/or the breathing report 165.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
   receiving, by a processing apparatus, a video stream of a subject;
   generating, by the processing apparatus, a vector time series that comprises a vector for each image frame of the video stream;
   estimating, by the processing apparatus, a breathing signal from the vector time series;
   determining, by the processing apparatus, one of a large-scale motion and a breathing event of the subject based on the breathing signal; and
   generating, by the processing apparatus, an alert if both no breathing event is identified and no large-scale motion of the subject is identified within an event time interval,
   wherein estimating the breathing signal comprises:
      decomposing a matrix X of a windowed video subsequence of the video stream into a sparse matrix S representing moving objects and a low rank matrix L representing non-moving objects;
      reconstructing a video stream of the moving objects from the sparse matrix S, wherein each pixel of the reconstructed video stream of the moving objects comprises one of a scalar time series and a vector time series; and
      measuring breathing events in the reconstructed video stream.

2. The method of claim 1, further comprising capturing the video stream using a bandpass filter in the range of 0.8-2.5 micrometers and with a Charge Coupled Device (CCD) tuned to 1.5 micrometers.

3. The method of claim 1, wherein generating the vector time series comprises dividing each image frame into regions and summing pixel values in each region as a pixel sum.

4. The method of claim 1, wherein generating the vector time series comprises dividing each image frame into regions and removing a signal mean in each region.

5. The method of claim 1, the method further comprising:
   generating a breathing report based at least in part on breathing events determined based on the breathing signal, wherein the breathing report comprises one or more of: a breath rate, a maximum inter-breath interval, a minimum inter-breath interval, inter-breath interval statistics, an inter-breath interval histogram, and apnea event data; and
   generating a motion report based at least in part on large-scale motions determined based on the breathing signal, wherein the motion report comprises one or more of: a motion frequency, a motion magnitude, a motion duration, a sleep length, a sleep quality, and sleep intervals.

6. The method of claim 1, wherein estimating the breathing signal comprises applying an adaptive subspace algorithm to each vector of the vector time series.

7. The method of claim 1, wherein estimating the breathing signal further comprises:
   defining a cursor t that indexes the image frames I of the video stream;
   defining a window length N;
   extracting the windowed video subsequence of the video stream comprising N image frames I(t−N+1), I(t−N+2), I(t−N+3), . . . , I(t−2), I(t−1), I(t); and
   organizing the windowed video subsequence into the matrix, X, having M rows and N columns, where M is the product of a height, a width and a number of channels in the image frames of the video stream.

8. The method of claim 7, the method further comprising:
   calculating a normalized auto-correlation for each pixel of the reconstructed video stream of moving objects; and
   identifying a breathing event in response to an auto-correlation peak for a given pixel of the reconstructed video stream of moving objects persisting over a specified number of consecutive time periods.

9. The method of claim 7, wherein the matrix X is decomposed by iteratively approximating a decomposition algorithm by:
   initializing S=0;
   calculating L=mean (X−S), wherein X=L+S+N and N is additive noise;
   calculating $$S\{i,j\}=\{X\{i,j\}-L\{i,j\}, \text{ if } \ldots X\{i,j\}-L\{i,j\} \cdot < T0, \text{otherwise}\},$$

wherein S{i,j} denotes the element of the matrix S on the ith row and the jth column, and T is a sparsity threshold; and
   repeating the calculating steps until a stopping condition is satisfied.

10. The method of claim 1, the method further comprises:
    encoding a breath rate from a plurality of breathing events as a heat map;
    overlaying the heat map on the video stream for display to a user.

11. The method of claim 1, the method further comprises:
    encoding large-scale motion of a subject as a heat map;
    overlaying the heat map on the video stream for display to a user.

12. An apparatus comprising:
one or more memory devices; and
one or more processing devices, in communication with the one or more memory devices, and configured to:
receive a video stream of a subject via a camera;
generate a vector time series that comprises a vector for each image frame of the video stream, estimate a breathing signal from the vector time series, and determine one of a large-scale motion and a breathing event of the subject based on the breathing signal; and
generate an alert if both no breathing event is identified and no large-scale motion of the subject is identified within an event time interval,
wherein estimating the breathing signal comprises:
decomposing a matrix X of a windowed video subsequence of the video stream into a sparse matrix S representing moving objects and a low rank matrix L representing non-moving objects;
reconstructing a video stream of the moving objects from the sparse matrix S, wherein each pixel of the reconstructed video stream of the moving objects comprises one of a scalar time series and a vector time series; and
measuring breathing events in the reconstructed video stream.

13. The apparatus of claim 12, further comprising a camera that comprises a bandpass filter in the range of 0.8-2.5 micrometers and a Charge Coupled Device (CCD) tuned to 1.5 micrometers.

14. The apparatus of claim 12, wherein generating the vector time series comprises dividing each image frame into regions and summing pixel values in each region as a pixel sum.

15. The apparatus of claim 12, wherein generating the vector time series comprises dividing each image frame into regions and removing a signal mean in each region.

16. The apparatus of claim 12, wherein the one or more processing devices are further configured to:
generate a breathing report based at least in part on breathing events determined based on the breathing signal, wherein the breathing report comprises one or more of: a breath rate, a maximum inter-breath interval, a minimum inter-breath interval, inter-breath interval statistics, an inter-breath interval histogram, and apnea event data; and
generate a motion report based at least in part on large-scale motions determined based on the breathing signal, wherein the motion report comprises one or more of: a motion frequency, a motion magnitude, a motion duration, a sleep length, a sleep quality, and sleep intervals.

17. The apparatus of claim 12, wherein estimating the breathing signal comprises applying an adaptive subspace algorithm to each vector of the vector time series.

18. The apparatus of claim 12, wherein estimating the breathing signal further comprises:
defining a cursor t that indexes the image frames I of the video stream;
defining a window length N;
extracting the windowed video subsequence of the video stream comprising N image frames I(t−N+1), I(t−N+2), I(t−N+3), . . . , I(t−2), I(t−1), I(t);
organizing the windowed video subsequence into the matrix, X, having M rows and N columns, where M is the product of a height, a width and a number of channels in the image frames of the video stream.

19. The apparatus of claim 17, wherein the one or more processing devices are further configured to:
calculate a normalized auto-correlation for each pixel of the reconstructed video stream of moving objects; and
identify a breathing event in response to an auto-correlation peak for a given pixel of the reconstructed video stream of moving objects persisting over a specified number of consecutive time periods.

20. The apparatus of claim 17, wherein the matrix X is decomposed by iteratively approximating a decomposition algorithm by:
initializing S=0;
calculating L=mean (X−S), wherein X=L+S+N and N is additive noise;
calculating $S\{i,j\}=\{X\{i,j\}-L\{i,j\},\text{ if }\ldots X\{i,j\}-L\{i,j\}\cdot <T0,\text{otherwise}\},$ wherein S{i,j} denotes the element of the matrix S on the ith row and the jth column, and T is a sparsity threshold; and
repeating the calculating steps until a stopping condition is satisfied.

21. The method of claim 1, further comprising:
calculating breathing data comprising one or more of: a breath rate, a maximum inter-breath interval, a minimum inter-breath interval, inter-breath interval statistics, and an inter-breath interval histogram; and
identifying a sleep apnea event based on the breathing data.

* * * * *